United States Patent
Craig et al.

(10) Patent No.: US 6,786,722 B2
(45) Date of Patent: Sep. 7, 2004

(54) ORTHODONTIC MODELING FILLER MATERIAL AND METHOD

(75) Inventors: Doris Craig, Hewitt, TX (US); Kammy Parker, Waco, TX (US)

(73) Assignee: Divine Inspirations, LLC, Waco, TX (US)

( * ) Notice: Subject to any disclaimer, the term of this patent is extended or adjusted under 35 U.S.C. 154(b) by 0 days.

(21) Appl. No.: 10/214,248

(22) Filed: Aug. 7, 2002

(65) Prior Publication Data

US 2002/0187456 A1 Dec. 12, 2002

Related U.S. Application Data

(63) Continuation-in-part of application No. 09/790,119, filed on Feb. 21, 2001, now abandoned.

(51) Int. Cl.[7] .................................................. A61C 9/00
(52) U.S. Cl. ......................................... 433/48; 433/213
(58) Field of Search .............................. 433/48, 45, 37, 433/213, 214

(56) References Cited

U.S. PATENT DOCUMENTS

| 3,360,860 | A | * | 1/1968 | Roland ......................... 433/45 |
| 4,386,964 | A | * | 6/1983 | Herbert .................... 106/132.2 |
| 4,529,384 | A | * | 7/1985 | Severy ........................ 433/213 |
| 5,538,551 | A | * | 7/1996 | Desbiens ................. 106/128.1 |
| 5,980,880 | A | * | 11/1999 | Love ......................... 424/76.1 |
| 6,318,997 | B1 | * | 11/2001 | Mayweather ................. 433/45 |

OTHER PUBLICATIONS

Mindrum, Beverly, "Bright Play Ideas for Rainy Days" Jul. 6, 1984, Miami Herald p. 1B.*

* cited by examiner

*Primary Examiner*—Kevin Shaver
*Assistant Examiner*—Melba Bumgarner
(74) *Attorney, Agent, or Firm*—David G. Henry

(57) ABSTRACT

A dough-like filler material and method of use thereof. The dough-like filler is used (in lieu of more expensive, less easily handled filler materials) in the process of making plaster dental molds for dental or orthodontic use to fill voids in dental impression molds, voids which otherwise would allow for the formation of obstructive plaster accumulations in the resulting plaster dental mold.

3 Claims, 1 Drawing Sheet

US 6,786,722 B2

ORTHODONTIC MODELING FILLER MATERIAL AND METHOD

This is a continuation-in-part of copending application(s) Ser. No. 09/790,119 filed on Feb. 21, 2001, now abandoned

BACKGROUND OF THE INVENTION

1. Field of the Invention

The present invention relates to orthodontic modeling methods and materials.

2. Background Information

As is the case with any service-based occupation, time is money in dentistry and orthodontics. Therefore, any method or product which expedites the delivery of services in the dental and orthodontics fields will translate into greater profitability for practitioners and, perhaps, lower cost of care for patients and insurance companies.

For a number of dental and orthodontic procedures, dental models or "impressions" are made. Models are made first by producing a rough, negative topological impression. This is taken with the assistance of a standard perforated metal or plastics tray, wherein for the impression material alginate, palgate, etc. are used. Then the topological impression is used to form a cast using hard plaster, which produces a positive topological model, which, in turn, reflects the rough topology found in the mouth or on the biting surfaces of the patient, i.e. existing or absent teeth, the shape of the jaw crest and the mucous membranes, irregularities, etc.

For certain procedures, a number of additional steps are involved, and include the creation of a negative topological tray or "functional tray", a precise topological or "functional" impression, a precise topological or "functional" model, and an occlusion mold or bite impression, all, in some cases, leading to the creation of a final denture, plate or other dental or orthodontic appliance. However, the step(s) in which impressions in trays are used to produce plaster casts are those processes with which the present product and method are concerned.

A consequence of the inevitable design of impression trays used to make lower teeth impressions is that a large space or void exists where the tray is contoured for receiving a patient's tongue during an impression step. If left unoccluded, this void will fill with plaster during the casting process—plaster which must later be painstakingly removed to acquire adequate access and visualization of the teeth in the resulting plaster model.

Some dental and orthodontic offices use alginate (the same material that is used as the actual impression) to fill this void in the lower impression tray and, thereby, partially avoid the excess plaster problem. This is not an efficient or cost-effective solution to the problem. Alginate is not forgiving of mixing errors, often sets up more quickly than is consistent with its use after an impression is taken and to fill the void in the lower teeth tray for casting, and is somewhat expensive. Other dental and orthodontic offices simply do nothing, and, after a plaster model is made, carefully trim away the excess plaster to gain access and visualization to the pertinent portions of the model. This latter approach is extremely time-consuming and even poses a potential health risk due to the dust produced by the plaster removal process.

Another, separate problem which arises in the context of making dental models relates to unintended gaps or voids in the plaster model which is produced as part of the progression to a final dental appliance.

When plaster models are produced, inevitably there are gaps and voids formed by bubbles, air pockets, molding technique mistakes, etc. In addition, certain gaps which are accurate reflections of the patient's mount or dental structures will be filled when making the plaster model for the ultimate production of dental appliances—missing natural teeth, for example.

Such gaps or voids must be filled and properly contoured before using the model for further development of a dental appliance. Otherwise, a new model must be made—a considerable waste of time and expense, and one sometimes involving calling the patient back into the dental office for a new impression.

In view of the above, it would be very beneficial to dental and orthodontic practitioners to provide a method and related product which can be used in avoiding the excess plaster problems which are inherent in the use of lower teeth impression trays, and which method and related product is simple to use, very cost-effective, environmentally benign, and at least as effective as any known method or product. In addition, it would likely, but independently well-serve such professionals to provide a method and associated material which could be used to quickly, conveniently and cost-effectively fill voids in plaster models, caused by bubbles, air pockets, etc. in order to avoid having to replace the defective models, or consume expensive materials which are difficult to work in this context.

SUMMARY OF THE INVENTION

In view of the foregoing, it is an object of the present invention to provide a filler material for use with dental model impression trays in occluding space which is otherwise filled with excess plaster during a plaster model casting process.

It is another object of the present invention to provide a method for producing a filler material which is useful in occluding spaces in dental impressions and appliances in which, without use of such filler material, unwanted plaster would reside after the plaster pouring step of making a dental impression, such process resulting in an optimally tacky dough-like material which is inexpensive to produce and purchase, is pre-mixed, requires no set up time, is water soluble for easy cleanup, is easy to form to any desired shape, has a very long shelf life, is environmentally benign, and which exhibits a desirable, slightly sticky or tacky quality which, unlike PLAYDOUGH-like products, will adhere to dental impression appliances to a degree necessary to remain in-place during use, but not so tacky as to be difficult to remove or for a user to disengage from hands and fingers.

It is another object of the present invention to provide a method by which space within the bounds of a lower teeth impression tray, which is otherwise filled with excess plaster during a plaster model casting process, is occluded with a convenient and cost-effective dough-like filler material thereby obviating the problems left unsolved in the prior art.

It is another object of the present invention to provide a method and associated material which could be used to quickly, conveniently and cost-effectively fill voids in plaster models, caused by bubbles, air pockets, etc. in order to avoid having to replace the defective models, or consume expensive materials which are difficult to work in this context.

The product of the present invention is a dough-like filler material which is used to temporarily occlude or occupy the space or void which is provided in the lower teeth impression tray for use in dental modeling for accommodating a patient's tongue. The dough-like filler material is used after an initial impression is taken and before plaster is applied to form a positive model. The presence of the dough-like filler material during the plaster casting process prevents the formation of plaster accumulations which interfere with access and visualization of the teeth portions of a plaster model.

Extensive development and research efforts by the present inventors reveals that not just any filler material will work. The formulation and method of producing the product in its present form is the result of countless variations of constituents and processing methods. Earlier formulae and/or processing methods resulted in filler which was too sticky, not sticky enough (would not stay in-place on impression appliances), was too stiff to work with, and/or lacked adequate shelf life to be a viable product for other than instantaneous use after making the product.

The use of the present dough-like filler material as described provides a highly cost-effective alternative to the prior art approaches of using alginate (or other impression material) to occlude the lower teeth tray void, or the use of no occluding material followed by manual carving away of excess plaster.

In addition to the foregoing, the present dough-like filler material can be used to quickly, conveniently and cost-effectively fill voids in plaster models, caused by bubbles, air pockets, etc. in order to avoid having to replace the defective models, or consume expensive materials which are difficult to work in this context.

The dough-like filler material of the present invention is, unlike conventional impression material, inexpensive to produce and purchase, is pre-mixed, requires no set up time, is water soluble for easy cleanup, is easy to form to any desired shape, has a very long shelf life, and is in environmentally benign. It furthermore exhibits a desirable, slightly sticky or tacky quality which, unlike PLAYDOUGH-like products, will adhere to dental impression appliances to a degree necessary to remain in-place during use, but not so tacky as to be difficult to remove or for a user to disengage from hands and fingers.

Practice of the present invention will save time and money in the dental and orthodontic practices and pull solve problems not heretofore solved by any known prior art approach.

DETAILED DESCRIPTION OF THE PREFERRED EMBODIMENT

Figure 1:
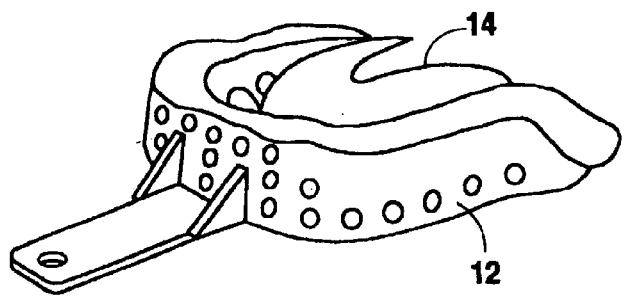
FIG. 1 is a perspective view of a dental impression tray prior to application of any of the filler material of the present invention.

The dough-like filler material of the present invention is easily formulated. Obviously, commercial production will require proportional scale up, but a single, 51 oz. batch "recipe" for the present filler is as follows:

3 cups standard baking flour
1½ cups salt
3 cups water
6 tbsp. cream of tartar
6 tbsp. vegetable cooking oil
15 drops peppermint oil
6 drops food color (optional)

According to conventional conversions, the above measurements can be converted as follows: 2 tablespoons=1 part by volume and 1 cup=8 parts by volume, with the measurements being given in drops being appropriately scaled-up based on the most basic of batch manufacturing experience.

The precise method of manufacture of the present filler material is, as mentioned before, the result of much experimentation and adjustment. The process, in its presently believed best mode (for making one 51 oz. batch, but scalable for larger batches) is as follows:

Mixing

1. Measure vegetable oil and water.
2. Add the food coloring to warm tap water (approximately 90°–100° F. [not substantially hotter or cooler], and stir thoroughly.
3. Pour the water and food coloring mixture into a mixing bowl appropriate to the size of the intended filler batch.
4. Add dry ingredients slowly and then stir completely.
5. Then add the vegetable oil.
6. Place the mixing bowl onto a commercial mixer stand (HOBART model A200 is exemplary for this method), attach its spiral whisk to the mixer, and latch mixing bowl on both sides.
7. Set timer for 30 seconds and mix ingredients on mixer's lowest speed.
8. Turn the mixer up to a higher, medium speed and mix for an additional minute.
9. Reset timer for 1 minute and mix on mixer's highest ($3^{rd}$ speed on a three or more speed mixer).
10. Stop the mixer and timer.
11. After the mixture is poured, scrape the excess from sides into the bottom of mixing bowl.

*Total mixing time: 2 minutes and 30 seconds.

Cooking

1. Set a commercial, flat-topped grill to 275° F. (assuring that grill is clean and does not have dried dough on it from prior batches).
2. Starting from the back of the grill pour mixture onto the grill from left to right and leave for 2 minutes and 45 seconds.
3. Turn product onto the other side and cut into 2 rows of squares the size of the spatula beginning on the row nearest person cooking. This should take approximately 1 minute to 1 minute and 15 seconds.
4. Then leave on the grill for 45 seconds.
5. Work into a ball for 45 seconds.
6. Then knead on grill for 1 minute and 15 seconds.

Kneading

1. Place a kneading bowl onto a kneading stand (HOBART model D330 is exemplary for the present method), attach the flat paddle style beater to the kneading machine, and latch kneading bowl on both sides.
2. Add aromatic (peppermint) oil to dough.
3. Set kneader to high (#3) speed and knead for 45 seconds.
4. Spread mixture out on packaging table for cooling, and allow to cool for 25 minutes.

** The kneading bowl must be cleaned after the sixth use and sprayed with vegetable cooking spray.

Packaging

Do Not Package Product Hot!!

1. Using the scale, weigh the product to 3 lbs. 4 oz.
2. Hand knead the product, form in a smooth ball, and lightly spray with vegetable oil cooking spray (such as PAM brand cooking spray) and spread around the formed ball.
3. Let product set for 30 seconds.
4. Place product in plastic bag and press down to remove air.
5. Close the bag.

It should be understood that variations in constituents, such as moisture in flour, ambient temperature in the manufacturing facility, water quality, etc. may require slight variations in cooking, kneading, and cooling times, as well as slight adjustments in relative volumes of constituents. However, such variations will be within the skills of any competent batch manufacturing supervisor or manager. Therefore, quantities and cooking, kneading and cooling times, while found to be optimal in working conditions of relatively normal range of temperature and humidity, and using constituents of standard quality (14% moisture in standard baking flour, for example), should, in other conditions or circumstances, be understood to be approximate. If adjusting cooking times for a minute one way or the other, or, for example, varying constituent amounts by a relative or so, should be required to meet other than standard conditions or circumstances to produce product of desirable characteristics, such should be understood to still fall within the scope of the present invention.

It should also be noted that the use of peppermint oil (or an equivalent aromatic oil, if such can be determined to truly be equivalent for present purposes) is not merely for aesthetic purposes. Experiments using and omitting the peppermint oil have revealed, contrary to earlier assumptions, that such is a vital component to the present filler material. When the peppermint oil is omitted, the filler exhibits noticeably inferior characteristics and shelf life performance. It is believed that the oil (particularly when added in the sequence discussed above) has some marked effect on moisture retension, thereby preserving optimal texture, and preventing "crystalization." It is suspected that wintergreen, spearmint, or even clove oils may perform equivalent functions to that of peppermint oil in this context, but such has not yet been determined at this time of this filing.

Use of Filler Material

Figure 2:
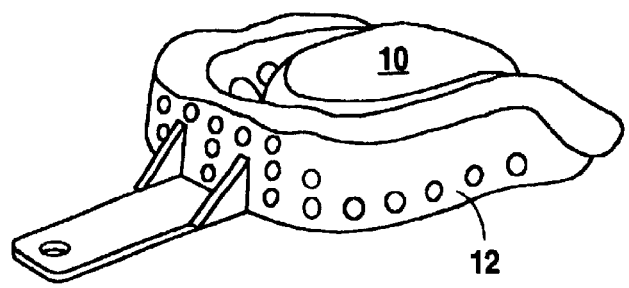
FIG. 2 is a perspective view of the impression tray of FIG. 1 with the filler material of the present invention applied to occlude the void otherwise present after the impression step.

Referring to FIG. 1, after an initial impression is taken, and impression tray 12 will include a void 14 where a patients tongue resided during the impression process. Referring to FIG. 2, the present filler material 10 is, according to the present invention, manually placed and formed to occlude the void 14. Filler material, properly manufactured according to the present invention, will remain in place after applying light pressure, but will not stick to one's hands under most circumstances. Once the filler material is in-place, the plaster casting step of dental modeling follows according to conventional processes.

Figure 3:
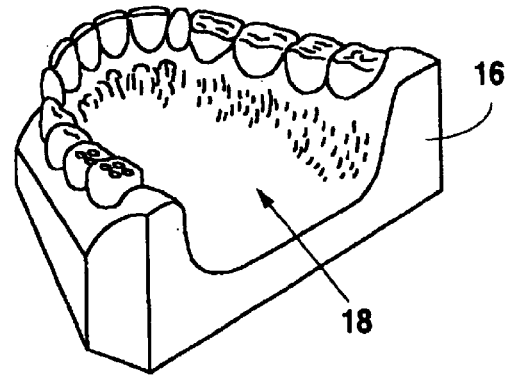
FIG. 3 is a perspective view of a plaster cast model showing a cavity left by the presence of the present filler material during the plaster casting process, a cavity otherwise filled with plaster had such a filler material not been used.

Referring to FIG. 3, a plaster model 16 is depicted and shows a large cavity 18. Cavity 18 is the product of filler material 10 having resided in void 14 of tray 12 during the plaster casting process. Had filler material 10 not been positioned as described, excess and obstructive plaster material would have occupied cavity 18 and prevented ready access and visualization of the interior surfaces of the teeth renditions of the plaster model 16.

Although not referenced in the drawings, the use of the subject filler material to fill voids in plaster dental models is an independently significant aspect of the present invention. Once a plaster dental model is created, if voids or holes are present, these must be filled and contoured to match that which the model should have replicated, but for the air gap or bubble which created the void or hole during the molding process. As with the use of the present filler material in lieu of alternative dental modeling materials which might otherwise be used to fill such voids, use of the present filler material to fill voids and holes in plaster dental models will save practitioners' time and money to a very significant degree. Use of alginate and the like in this context poses the same problems and objections as in using it to fill the tongue void in a lower dental impression as discussed above.

The use of filler material 10 in the described contexts obviate a number of problems as already described. Filler material 10 is either substantially odor free or pleasantly scented. Once mixed, and if kept any sealed container, filler 10 exhibits a very long shelf life, if the vegetable oil cooking spray (or like material) is used. Whether used to fill cavity 18, or to fill gaps, voids, or to create structures where none existed (missing teeth) the use of filler material 10 renders the resulting models 16 more useful and accurate than models made without the use of such a void occluding material, without excessive lab technician contouring and carving time.

Although the invention has been described with reference to specific embodiments, this description is not meant to be construed in a limited sense. Various modifications of the disclosed embodiments, as well as alternative embodiments of the inventions will become apparent to persons skilled in the art upon the reference to the description of the invention. It is, therefore, contemplated that the appended claims will cover such modifications that fall within the scope of the invention.

I claim:

1. A method for producing and finishing a plaster dental model comprising the steps of:

making a dental impression for use of a impression material-filled impression tray, said impression tray having a void for accommodating a patient's tongue;

applying a plaster material to said dental impression for producing a plaster dental mold;

upon curing of said plaster dental model, filling undesirable voids in said plaster dental model with a dough-like filler material comprising constituents of approximately the ratios of:

24 parts flour by volume;
   12 parts salt by volume;
   24 parts water by volume;
   3 part cream of tartar; and
   3 part cooking oil;

said constituents being blended to form a substantially uniform consistency and texture; said constituents being cooked at an elevated temperature, followed by kneading and cooling before packaging.

2. The method of claim 1 wherein said filler material further comprising a measure of aromatic oil.

3. The method of claim 2 wherein said aromatic oil is peppermint oil.

* * * * *